US009228928B2

(12) United States Patent  
Mauvoisin

(10) Patent No.: US 9,228,928 B2  
(45) Date of Patent: Jan. 5, 2016

(54) CONTINUOUS OR INSTRUMENTED INDENTATION DEVICE

(75) Inventor: Gérard Mauvoisin, Chantepie (FR)

(73) Assignee: UNIVERSITE DE RENNES 1, Rennes (FR)

( * ) Notice: Subject to any disclaimer, the term of this patent is extended or adjusted under 35 U.S.C. 154(b) by 610 days.

(21) Appl. No.: 13/512,807

(22) PCT Filed: Nov. 30, 2010

(86) PCT No.: PCT/FR2010/052571  
§ 371 (c)(1),  
(2), (4) Date: Aug. 15, 2012

(87) PCT Pub. No.: WO2011/064517  
PCT Pub. Date: Jun. 3, 2011

(65) Prior Publication Data  
US 2012/0304750 A1  Dec. 6, 2012

(30) Foreign Application Priority Data

Nov. 30, 2009 (FR) ...................................... 09 05737

(51) Int. Cl.  
*G01N 3/42* (2006.01)

(52) U.S. Cl.  
CPC .......... *G01N 3/42* (2013.01); *G01N 2203/0682* (2013.01)

(58) Field of Classification Search  
CPC .......................... G01N 3/42; G01N 2203/0098  
USPC .................................................. 73/81, 82, 85  
See application file for complete search history.

(56) References Cited

U.S. PATENT DOCUMENTS

| 4,023,401 A | 5/1977 | Ernst |
| 4,820,051 A * | 4/1989 | Yanagisawa et al. ......... 356/626 |
| 5,639,969 A * | 6/1997 | D'Adamo ....................... 73/818 |
| 6,718,820 B2 * | 4/2004 | Kwon et al. ..................... 73/81 |

(Continued)

FOREIGN PATENT DOCUMENTS

| DE | 93 10 043 U1 | 9/1993 |
| DE | 92 18 581 U1 | 9/1994 |

(Continued)

OTHER PUBLICATIONS

International Search Report (PCT/ISA/210) issued on Feb. 21, 2011, by the French Patent Office as the International Searching Authority for International Application No. PCT/FR2010/052571.

*Primary Examiner* — Hezron E Williams  
*Assistant Examiner* — David Z Huang  
(74) *Attorney, Agent, or Firm* — Buchanan Ingersoll & Rooney PC

(57) ABSTRACT

This invention relates to a new portable device with no solid frame, which makes it possible to carry out instrumented indentation of a material to deduct its mechanical properties. Continuous or instrumented indentation consists in measuring the force and displacement when an indenter is pushed into the tested material. The device is made up of a sleeve with a reduced volume and its lower base, which may be of variable shapes adapted to that of the material to test, a piston sliding in the sleeve, the displacement of which is controlled by the hand of a user, a manipulating arm, a mechanical column or a robot, an elastic ring or a spring limiting the displacement of the piston, three displacement sensors arranged in an equilateral triangle around a single-piece indenter having any shape, and a force sensor that makes it possible to measure the change in the force depending on the depression made by the indenter in the tested material.

9 Claims, 3 Drawing Sheets

(56) References Cited

U.S. PATENT DOCUMENTS

| | | |
|---|---|---|
| 2005/0016264 A1 | 1/2005 | Anthe et al. |
| 2007/0157710 A1* | 7/2007 | Isomoto .............................. 73/81 |
| 2009/0260427 A1* | 10/2009 | Woirgard et al. .................. 73/85 |

FOREIGN PATENT DOCUMENTS

| | | |
|---|---|---|
| DE | 93 18 389 U1 | 3/1995 |
| DE | 202 12 026 U1 | 2/2003 |
| FR | 2 304 075 A1 | 10/1976 |
| FR | 2 823 307 A1 | 10/2002 |
| JP | 2007-327263 A | 12/2007 |
| WO | WO 03/056303 A1 | 7/2003 |
| WO | WO 03/073072 A1 | 9/2003 |
| WO | WO 2006/136038 A1 | 12/2006 |
| WO | WO 2008/156515 A2 | 12/2008 |

* cited by examiner

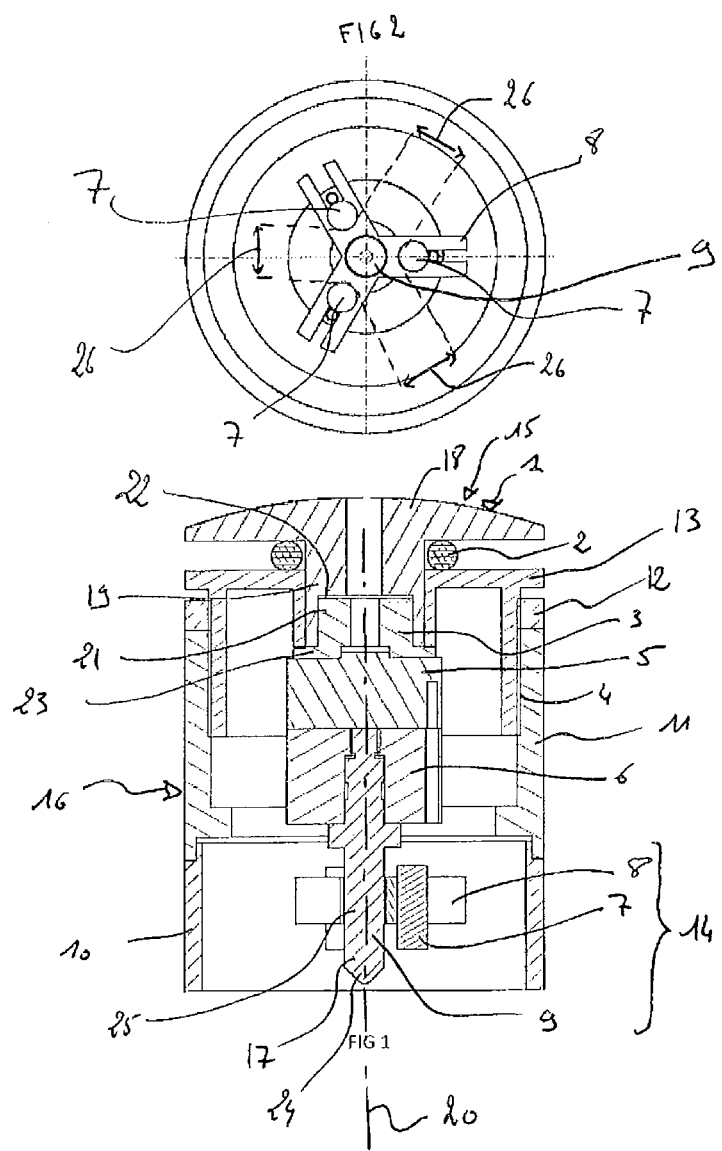

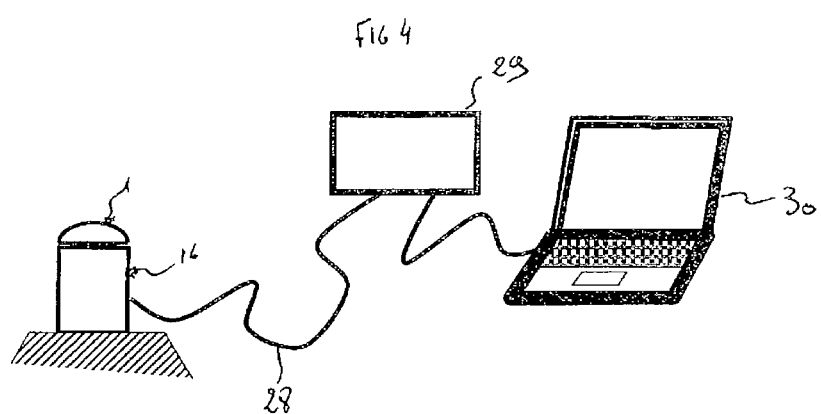

CONTINUOUS OR INSTRUMENTED INDENTATION DEVICE

This invention relates to a new portable device with no solid frame, which makes it possible to carry out instrumented indentation of a material to deduct its mechanical properties. Continuous or instrumented indentation consists in measuring the force and displacement when the indenter is pushed into the tested material.

The priority study has not revealed any device close to the device described as part of the invention presented here. It must be noted that there are a certain number of portable apparatuses for measuring hardness, including patents No. 76 06798 (hand-operated hardness measuring apparatus), No. WO2006/136038 A1 (Apparatus for Hardness Measurement by impact), No. WO03/056303 A1 (Hardness measuring device comprising a housing and a penetration body, in particular a manual device).

The indentation test is clearly different from the hardness test which firsts involves applying, for approximately 10 seconds, a load (dead weight) on an indenter in contact with the tested surface, and then measuring the size of the mark left on the surface of the material after the load is removed.

Thus, even though the hardness of materials can be identified by instrumented indentation, hardness meters do not allow the achievement of the mechanical properties that can be achieved by continuous or instrumented indentation.

Indentation is a valuable test for researchers and for industry, as it makes it possible to mechanically characterise a material in a short time on the nanometric, micrometric and macrometric scales. Current devices make it possible to make continuous or instrumented indentations while recording the force F depending on the depression h made by the indenter in the material. The indentation curve marked F(h), including the loading step and then the unloading step, depends on many experimental parameters and on mechanical properties. Once the experimental parameters are controlled and fixed, the indentation curve is characteristic of the material. It can be used to determine the parameters of the material behaviour law, usually obtained by the tensile test, which is destructive and which makes it necessary to have a certain volume of material to make a special standardised specimen. For its part, the indentation test is non-destructive, only needs a small volume of material and requires no special specimen. The indentation test is a very local test, which can be used to test very fine layers.

The inventor has designed and made their own indentation bench after finding problems in the reproducibility of the results and the reliability of the machines available in the market. It has been found that the displacement sensors on the test benches available in the market integrate into their measurements displacements that are due to the deformation of some parts of the test bench. Further, it has been observed that the experimental curves obtained with metal materials, the behaviour law of which has been obtained by a tensile test, do not match the numerical curves obtained using the finite-element method. The experimental curves are always found to be not as rigid as numerical curves, that is to say that for the same force, the displacement measured is always greater than that given by the finite-element method. That observation can be made on all the test benches in the market tested by the inventor, regardless of the material. There are two sources of error in the measurement of the depression.

The first source of error is due to the fact that in practice, the depression, which is the displacement of the lowest point of the indenter, is not measured directly but deduced from the displacement measured, in the best case, between the indenter and the sample. Different variably satisfactory solutions have been found. Most solutions integrate into the measured value displacements relating to the deformation of some elements of the frame, or displacements due to geometric faults of the test bench.

The second source of error is due to the use of indenters available in the market, which are originally designed for determining hardness from the mark left in the material after a load is applied and then removed. The indenters are made up of a diamond or tungsten carbide tip that is cut to a geometry depending upon the type of hardness test, crimped and/or glued in a cylindrical steel support, with one end that depends on the mode of fastening to the test bench. Crimping puts into contact two surfaces that never follow each other sufficiently well to avoid displacements at the interface between the tip and its support. Displacements are always fairly small but never negligible in view of the very small quantities involved. The geometric characteristics of the surfaces (including roughness) in contact are unknown to the user, and no modelling is possible to determine the displacements involved when the tip is brought close to its support during the test.

To conclude, these two sources of error do not make it possible to assimilate the displacement measured with the actual depression made by the indenter. But the knowledge of the actual depression is indispensable to determine the mechanical characteristics of the material. For example, the hardness H of the material can be determined from the depression made with the maximum load applied. The reduced modulus $E^*$ can also be determined according to the method of Oliver and Pharr, using the gradient (dF/dh) of the curve F(h) at the start of unloading [1]. Several methods also make it possible to determine the elastic limit of the material and one or more strain-hardening parameters. These methods are based on some quantities extracted from the indentation curve such as the curvature, elastic energy, plastic energy, total energy or the ratio between the plastic energy and the total energy. All these quantities depend on the depression h. The first solution selected by manufacturers of indentation devices consists in offering systems with very rigid frames, which are thus often solid and not portable, and which are not significantly deformed during the indentation test. The parts to test must thus be brought to these devices, which limits the field of application to parts that are easy to handle and come from a non-toxic environment. To eliminate the problem of parasite deformations, the complementary solution offered by manufacturers consists in applying an overall correction calculated from a non-universal calibration curve obtained by testing on reference materials. That overall correction requires significant calibration tests, which are not transferable from one material to another, and it is generally implemented in the measurement interpretation software and is not accessible to the user.

The device according to the invention makes it possible to remedy these drawbacks. It uses a new arrangement of displacement sensors and a single-piece indenter that make it possible to do away with the use of a rigid and solid frame, giving it the property of portability and opening new fields of application for indentation testing, such as that of solid parts or parts from a toxic environment. The invention relies on a clever assembly consisting in an indenting head that is designed to measure the actual depression made by the indenter, which eliminates the effect of the deformation of elements located above the indenter and below the tested part.

To that end, the continuous or instrumented indentation testing device according to the invention comprises an exterior support, a piston slidingly mounted in the said exterior support and comprising an indenter, means to dampen and regulate the force applied to the piston, an indenter displacement measurement system and a force measurement system that make it possible to measure the change in the force depending on the depression made by the indenter in the tested material, characterised in that the indenter is made of a single piece, a displacement measurement system support being mounted on the said single-piece indenter, the displacement measurement system being mounted on the said displacement measurement system support and integral with the said single-piece indenter when it is displaced.

In a perfected form, the device according to the invention comprises a removable lower base that is mounted on a sleeve of the exterior support, the said removable base being mounted between the said sleeve and the surface of the part to test. Advantageously, the lower base has a shape complementary to the tested part, the indenter sliding along an axis orthogonal to the surface of the tested material in the said lower base. Preferably, the lower base is transparent. In order to guarantee that the device is correctly held on a metal test piece, the lower base may comprise a magnetic element.

The displacement of the piston according to the invention, that is its sliding in the exterior support, is preferably controlled by the hand of a user, a manipulating arm, a mechanical column or a robot. In one embodiment, the device according to the invention is mounted on an automated mechanical element as part of a manufacturing line. In a perfected form, the invention relates to an indentation test device comprising an automated system such as a robot, mechanical arm or other system on which the piston according to the invention is installed.

The means for damping and regulating the force applied on the piston may for example be an elastic ring, a spring or any other speed regulating damper in order to achieve regular acquisition of the force applied to the piston.

In a preferential embodiment, the device according to the invention comprises a combination of displacement measurement systems distributed evenly around the indenter, for example three displacement measurement systems arranged in an equilateral triangle around the indenter.

Advantageously, the device according to the invention does not have a solid frame, that is to say it can be transported and used with only one hand.

The device according to the invention may be made with no force measurement system, for example as part of a hardness test.

This invention is now described with the help of examples that merely illustrate the scope of the invention, but are not limitative in any way, by reference to the illustrations enclosed, wherein:

FIG. 1 is a longitudinal sectional view of the device according to the invention;

FIG. 2 is a transverse sectional view of the indenter of the device according to the invention;

FIG. 4 is a schematic view of the device according to the invention integrated with an outside analysis system;

Figure 3:
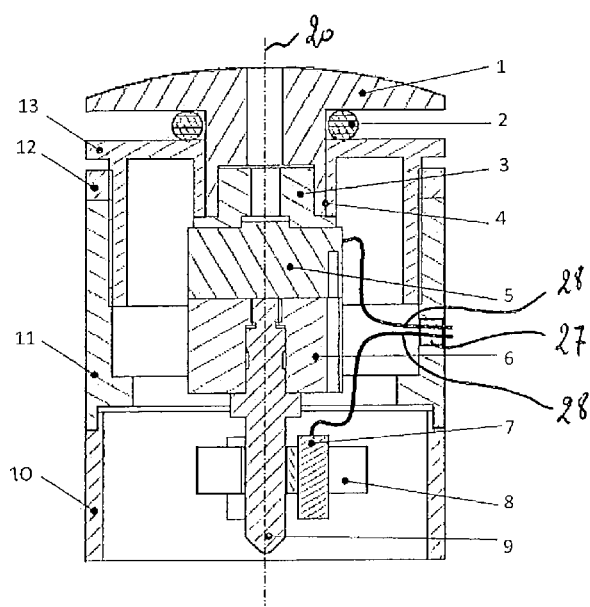
FIG. 3 is a longitudinal sectional view of the device according to the invention connected to an outside analysis element.

A list of the references used below in the description and the associated figures is given below:

1. Button
2. Means for regulating displacement and force
3. Adapting spacer
4. Sliding adjustment or ball guide
5. Force measurement system
6. Indenter support
7. Displacement measurement system
8. Support of displacement measurement system 7
9. Single-piece indenter
10. Lower base
11. Sleeve
12. blocking means
13. Upper flange
14. Indenting head
15. Piston
16. Exterior support
17. Lower end of indenter 9
18. Upper section of button 1
19. Lower section of button 1
20. Sliding axis of piston 15
21. Upper section of spacer 3
22. Hollow of the lower section 19 of button 1
23. Lower section of spacer 3
24. Tip of the single-piece indenter 9
25. Body of the single-piece indenter 9
26. Distance between two consecutive displacement measurement systems
27. Opening in sleeve 11
28. Connecting cable
29. Electronic unit
30. Computer In the description below, the term "longitudinal" means the longer side of an element, and "lateral" means the shorter side of an element. The "height", the adjective "upper" and the adjective "lower" relating to an element are used in respect of the normal installation of the device, that is to say relative to the vertical in relation to a horizontal flat floor on which the device according to the invention is placed, the indenter being then opposite the floor. The terms "distal" and "proximal" are used to characterise the remote part of a body or a main connection of the characterised element or the near part of the said body or main connection of the characterised element respectively.

FIG. 1 represents a longitudinal sectional view of the device according to the invention.

The device according to the invention comprises an exterior support 16 in which is slidingly mounted a piston 15, at the end of which is mounted an indenting head 14. During use, the device is placed on or fixed to the tested material, with the indenting head 14 opposite the tested material but not in contact. When the piston 15 slides in the exterior support 16 towards the material, that leads to the application of a thrust by the indenting head 14 on the material, typically the depression required for the indentation test.

The indenting head 14 is made up of an indenter 9 that is made up of a single piece, for example in the form of a single-piece 9 solid machined tungsten carbide indenter 9. A displacement measurement system support 8 is fixed to the indenter 9. Such a displacement measurement system support 8 acts as the assembly point for a displacement measurement system 7. Such a displacement measurement system 7 is for example a displacement feeler 7 or sensor 7 capable of determining the displacement of the indenter 9 and particularly the depression by the said indenter 9 in the material to test. The description below refers to a displacement measurement system 7 in the form of a sensor 7 for practical reasons, it being understood that such a sensor 7 is given as an example and that the invention relates to any displacement measurement system 7.

Preferably, three sensors 7 are mounted on the said sensor support 8.

Advantageously, these three sensors 7 are placed at 120° on the sensor support 8 around the indenter 9. A variable number of sensors 7 may be mounted on the support 8, the said sensors 7 being distributed on the support 8 evenly, that is to say that the distance 26 between two consecutive sensors 7 around the indenter 9 is identical for all the said sensors 7 placed on the support 8. In order to ensure the consistency of the results obtained by the combination of sensors 7, the said sensors 7 are located at an equal distance from the sliding axis of the indenter 9, that is to say the sliding axis 20 of the piston 15. The sensors 7 are placed very close to the lower end 17 of the indenter 9. Such sensors 7 are displacement sensors 7 capable of determining the displacement completed by the indenter 9 during an indentation test. Such sensors 7 are of any type known to those skilled in the art and all their component elements are preferably mounted on the sensor support 8.

The piston 15 is made of the following here:
- a button 1 that allows the user to apply the force required for the indentation test with their palm. The button 1 has an upper pushing section 18 that is complementary with an outside pushing element such as a hand of the user or a mechanical arm. The button 1 also comprises a circular cylindrical lower section 19 with a development direction identical to the sliding axis 20 of the piston 15 in the exterior support 16;
- the adapting spacer 3, which is an assembly part between the force measurement system 5 and the lower section 19 of the button 1. The adapting spacer 3 has a complementary shape, firstly with the lower section 19 of the button 1 and secondly with a force measurement system 5. Such a spacer 3 makes it possible to transmit to the force measurement system 5 the force applied to the button 1. In the example described in FIG. 1, the spacer 3 comprises a circular upper section 21 that is complementary with a hollow 22 of the lower section 19 of the button 1 in order to ensure effective cooperation and transmission of the force between the said button 1 and the spacer 3, the said upper section 21 of the spacer 3 being mounted in the said hollow 22. The spacer 3 further comprises a circular lower section 23 that is complementary and cooperates firstly with the force measurement system 5 and secondly with the lower section 19 of the button 1, ensuring effective transmission of the force between the spacer 3 and the force measurement system 5.
- the force measurement system 5. Such a force measurement system, for example a force sensor, analyses the force applied during the indentation test. The results of such an analysis can be sent to a computing unit, for example in order to allow the determination of the curve F(h) or any other mechanical information required about the tested material by the said computing unit.
- The indenter support 6, on which the indenting head 14 is fixed, providing a rigid connection between the indenter 9 and the force measurement system 5. The indenter support 6 is directly mounted on the force measurement system 5 by the complementary nature of the shapes of the said indenter support 6 and the said force measurement system 5, which transmits the forces sensed by the force measurement system 5 to the indenting head 14.
- the aforementioned indenting head 14, made up of the parts with the references 7, 8 and 9

The exterior support 16 is advantageously made up of 4 parts:
- the upper flange 13 that makes the sliding connection (sliding pivot connection) between the mobile piston 15 and the immobile exterior support 16 during the test. Such sliding is possible thanks to close sliding adjustment referenced 4 that could be replaced by a ball bushing or any other system that will allow the piston 15 to slide with guidance in the exterior support 16. Typically, the button 1 of the piston 15 is inserted to slide in the flange 13.
- the sleeve 11, the upper part of which is tapped in order to make the screw and nut connection with the upper flange 13, which makes it possible to adjust the height of the indenter 9 in relation to the surface of the tested material. On its outer surface, the upper flange 13 has a thread that cooperates with the sleeve 11 by screwing. Depending on the extent to which the flange 13 is screwed onto the sleeve 11, the piston 15 advances to a varying extent in the said sleeve 11 and thus the indenting head 14 is at a varying distance from the surface of the tested part when the device is installed.
- the knurled lock nut ring 12, which is used to lock the relative position between the upper flange 13 and the sleeve 11. Typically, the ring 12 locks the flange 13 into the sleeve 11 by tightening, the tightening of the ring 12 preventing the flange 13 to be screwed or unscrewed from the sleeve 11 and thus locking the relative positions of the flange 13 in relation to the sleeve 11,
- the lower base 10, which may possibly be made of transparent material of the Plexiglas type to aim the point to test, is placed on the part being tested. The base 10 is located between the sleeve 11 and the tested part. That interchangeable base may have a shape adapted to the part to test. Interchangeability may be achieved by any mounting means known to those skilled in the art, for example the upper part of the base 10 may comprise a thread that cooperates with a tap provided on the sleeve 11. In order to adapt to the part to test, the shape of the base 10 may vary both in its height, that is along the sliding axis of the piston, and in the shape of its lower part, so as to adapt to and cooperate with the part to test as much as possible. For example:
  - If the part to test is small in size, the base 10 may be a conical nozzle to rest on a small surface of the part, the lower part of the base 10 in contact with the part to test having the smaller diameter of the said base 10.
  - If the part to test is cylindrical, the lower part of the base 10 may have a V-shaped groove to facilitate positioning, the said V-shaped groove following the outer shape of the cylindrical part.
  - For complex sample surfaces, the lower part of the base 10 may be shaped like a tulip in order to ensure support contact at 3 points.
  - For a metal part, the base may be magnetic to maintain the position of the device during the indentation test.

This embodiment of the exterior support 16 is the preferred embodiment of the device according to the invention, the invention relating to a device that may comprise all these characteristics alone or in a combination. The invention may thus be made with a sleeve 11 integrating the flange 13, the piston 15 sliding directly in the sleeve 11. Similarly, the base 10 and the sleeve 11 may be made in a single piece.

The exterior support 16, which is simple and lightweight and fits in the hand, allows the guided displacement or sliding of the piston 15 towards the tested material with the help of the flange 13. That displacement movement may be guided by the user's hand, a mechanical column or arm or a robot, and is sufficient for a continuous indentation test. The movement is limited by the presence of the means 2 for damping and regulating the displacement and the force. The damping and regulating means 2 may for example take the form of an elastic ring 2, a spring 2, or any other means for damping and regulating the force and the depression that can ensure regular acquisition of the force applied to the piston. Such means 2 are particularly useful if the force is applied by the arm of a user, as such force is rarely applied evenly and regularly during the displacement of the piston. Such damping and regulating means 2 may be located between the exterior support 16 and the piston 15, typically between the flange 13 and the upper section 18 of the button 1 or at the sliding adjustment 4. Such regulating means 2 make it possible to maintain the indenting head 14 without contact with the tested piece when the device is installed on a piece to test.

In the absence of the damping and regulating means 2, in order to give the piston 15 sufficient freedom to slide so as to carry out the test, only supporting contact between the part to test and the indenting head 14 would make it possible to maintain the piston sufficiently back in the exterior support 16 to allow the free sliding required to displace the indenter 9 in all situations. However, such contact would lead to a significant loss of data, the contact alone being capable of generating deformations or the marking of the part to test. For example, as part of a test of a foam element, the mere weight of the piston 15 would be sufficient to push the indenting head 14 into the said foam element. It is thus necessary to keep a distance between the indenting head 14 and the tested piece, while giving the piston 15 sufficient freedom to slide in the exterior support 16 so as to carry out the test. The device according to the invention allows that by the presence of the said damping and regulating means 2.

FIG. 2 is a transverse sectional view of the indenter of the device according to the invention.

The indenter 9, including a tip 24, made in any shape adapted to the test, and a body 25 of the said indenter 9, is machined in a tungsten carbide block. There is thus no displacement between the tip 24 and the body 25 of the indenter 9. The indenter 9 may be deformed elastically under a load, but the corresponding displacements are very small as tungsten carbide is very rigid (E=600 GPa). However, the displacement between the sensor support 8 and the lowest point of the indenter 9 can be calculated easily from the Young's modulus, the simple geometry of the indenter 9 and the radius of contact between the indenter and the tested material [2].

The device according to the invention comprises at least one displacement feeler or sensor 7 to sense the indenting head 14, such as a capacitive sensor. According to the invention, that sensor 7 is mounted on a sensor support 8. The sensor support 8 according to the invention is mounted directly on the indenter 9. The sensor 7 preferentially comprises all the elements capable of determining the displacement of the indenter 9 installed on the said sensor support 8, no element installed for example on the exterior support 16 being involved in the determination of the displacement of the indenter 9. The sensor 7 is displaced integrally with the indenter 9. The single-piece design of the indenter 9 associated with the installation of the sensor 7 directly on the indenter 9 allows the accurate and disturbance-free determination of the actual displacement of the indenter 9 in relation to the part to test, that is the depression made by indenter 9 in the said part to test.

The sensor support 8 preferably allows the installation of a combination of sensors 7. For example, three displacement sensors 7 are installed on the sensor support 8 so as to be integral with the displacement of the indenter 9. The sensors 7 are distributed evenly over the sensor support 8 around the indenter 9, that is to say the distance 26 between two consecutive sensors 7 around the indenter 9 is the same for all the sensors 7. Thus, if three sensors 7 are mounted on the sensor support 8, the three displacement sensors 7 form an equilateral triangle, at the centre of which is positioned the single-piece indenter 9. Further, each sensor 7 is mounted on the support 8 at an equal distance from the sliding axis of the indenter 9.

The sensors 7 sense the surface of the tested material. The deformations of the elements located below the sample to test and above the indenter 9 can slightly affect the direction of the axis of the indenter 9 and/or the support of the sample to test. The sensors 7 do not then provide the same measurements but the average of the three measurements is the actual distance between the indenter 9 and the tested material. Thus, the deformations of the exterior support 16, the piston 15 and the sample support do not disrupt the proposed measurement system.

The simple and clever assembly presented above overcomes the problem of the deformations of elements of the indentation test benches that are currently used, which usually disturb the measurement of the actual depression made by the indenter 9.

The invention makes it possible to overcome the problem of the deformations above the indenter 9 by making the sensor or sensors 7 integral with the displacement of the indenter 9 which is made in a single piece, and those below the sample by the presence of several displacement sensors 7 that even out the results of the displacement of the indenter obtained by the sensors 7, unlike the usual design of continuous indentation benches, which require rigid frames to minimise the effect of deformations. As a result, a simple mechanical body that allows the guided displacement of the piston 15 comprising the indenting head is sufficient for a continuous indentation test. The size of the invention is so small that the system can fit in the hand, and is worthy of the description "portable". This is only one example out of the several that may be made with this indenting head.

FIG. 3 is a longitudinal sectional view of the device according to the invention connected to an outside analysis element.

In this example of embodiment, an opening 27 is made in the sleeve 11 so as to allow the passage of cables 28 connected to an outside analysis element. These cables 28 are firstly connected to the said outside element, and secondly to the different sensors of the device according to the invention, that is the force measurement system 5 and the displacement sensor or sensors 7.

FIG. 4 is a schematic view of the device according to the invention integrated with an exterior analysis system.

Preferably, the continuous indentation test device is connected to an electronic unit 29 that makes it possible to convert and transmit the measured quantities continuously to a computer 30. Such a computer 30 comprises programs for analysing and computing the results. Such a computer may also comprise a program for controlling the device.

Further, the device according to the invention may also be used for a hardness test, the device according to the invention being then simply made by direct connection between the indenting head 14 and the button 1 and/or the adapting spacer 3. A simple measurement of the depression after the application of a load, determined beforehand, on the button makes it possible to obtain the results of such a hardness test.

Besides, when used with a robot or a mechanical arm, the piston 15 according to the invention can be guided directly by the said robot or mechanical arm, the device according to the invention no longer needing in that case to comprise the exterior support 16.

POSSIBLE INDUSTRIAL APPLICATIONS

The device made in this manner may be used for the in-situ measurement of the mechanical characteristics of materials such as hardness, Young's modulus, elastic limit, strain hardening exponent etc.

REFERENCES

Patents No. 76 06798: hand-operated hardness measurement apparatus

Patent No. WO2006/136038 A1: Apparatus for Hardness Measurement by impact

Patent No. WO03/056303 A1: Hardness measuring device comprising a housing and a penetration body, in particular a manual device.

[1] Oliver, W. C., Pharr, G. M., 1992. An improved technique for determining hardness and elastic modulus using load and displacement sensing indentation experiments. J. Mat. Research 7 (6), 1564-1583.

[2] Collin, J-M., Mauvoisin, G., El Abdi, R., An experimental method to determine the contact radius changes during a spherical instrumented indentation, Mechanics of Materials (2007), doi: 10.1016/j.mechmat.2007.10.002

The invention claimed is:

1. A continuous or instrumented indentation testing device comprising an exterior support, a piston slidingly mounted in the said exterior support and comprising an indenter, means for damping and regulating a force applied to the piston, a displacement measurement system and a force measurement system wherein the indenter is made of a single piece, a displacement measurement system support being directly mounted on the said indenter, the displacement measurement system being mounted on the said displacement measurement system support and integral with the said single-piece indenter when the indenter is displaced, so that the displacement measurement system is linked to displacement of the indenter, the indentation testing device further comprising a removable lower base that is mounted on a sleeve of the exterior support, the removable lower base being mounted between the sleeve and a surface of a part that is tested with the indentation testing device, the removable lower base having a shape complementary to the part that is tested, the indenter sliding along an axis orthogonal to the surface of the part that is tested, and the indentation testing device does not have a solid frame.

2. The device according to claim 1, wherein the displacement of the piston is controlled by the hand of a user, a manipulating arm, a mechanical column, or a robot.

3. The device according to claim 1, wherein the means for damping and regulating the force applied to the piston is one of an elastic ring and a spring.

4. The device according to claim 1, further comprising a combination of displacement measurement systems distributed evenly around the indenter.

5. The device according to claim 1, further comprising two additional displacement measurement systems, wherein the displacement measurement system and the two additional measurement systems are arranged in an equilateral triangle around the indenter.

6. The device according to claim 1, wherein the device is mounted on an automated mechanical element as part of a manufacturing line.

7. The continuous or instrumented indentation testing device according to claim 1, wherein the lower base is transparent.

8. The continuous or instrumented indentation testing device according to claim 1, wherein the lower base comprises a magnetic element.

9. The continuous or instrumented indentation testing device according to claim 1, further comprising an automated displacement system associated with a piston.

* * * * *